(12) United States Patent
Visser et al.

(10) Patent No.: US 10,815,503 B2
(45) Date of Patent: Oct. 27, 2020

(54) PROCESS FOR MANUFACTURING PROPIONATE PRODUCTS

(71) Applicant: PURAC BIOCHEM BV, Gorinchem (NL)

(72) Inventors: Diana Visser, Gorinchem (NL); Jasper Meijer, Gorinchem (NL); Filipa Cristina Soares Mendes, Gorinchem (NL)

(73) Assignee: PURAC BIOCHEM BV, Gorinchem (NL)

( * ) Notice: Subject to any disclaimer, the term of this patent is extended or adjusted under 35 U.S.C. 154(b) by 110 days.

(21) Appl. No.: 15/558,842

(22) PCT Filed: Mar. 17, 2016

(86) PCT No.: PCT/EP2016/055753
§ 371 (c)(1),
(2) Date: Sep. 15, 2017

(87) PCT Pub. No.: WO2016/146721
PCT Pub. Date: Sep. 22, 2016

(65) Prior Publication Data
US 2018/0073044 A1 Mar. 15, 2018

(30) Foreign Application Priority Data
Mar. 18, 2015 (EP) .................................... 15159568

(51) Int. Cl.
*C12P 7/52* (2006.01)
(52) U.S. Cl.
CPC ..................................... *C12P 7/52* (2013.01)
(58) Field of Classification Search
CPC ........................................................ C12P 7/52
USPC ............................................................ 426/7
See application file for complete search history.

(56) References Cited

U.S. PATENT DOCUMENTS 4,700,000 A * 10/1987 Merkel ................. C07C 51/412
562/606

FOREIGN PATENT DOCUMENTS

CA        2058438 A1    10/1991

OTHER PUBLICATIONS

Martinez-Campos, R. et al. Biotechnol. Lett. 24: 427-431 (2002) (Year: 2002).*
Zhu, Y. et al. Bioresource Technol. 101: 8902-8906 (2010) (Year: 2010).*
Dishisha et al. "Improved propionic acid production from glycerol: Combining cyclic batch- and sequential batch fermentations with optimal nutrient composition.", Bioresource Tehcnology, vol. 176, 2015, pp. 80-87.
Stowers et al. "Development of an Industrializable Fermentation Process for Propionic Acid Production." Journal of Industrial Microbiology and Biotechnology, vol. 41, 2014, pp. 837-852.
Dishisha et al. "An Economical Biorefinery Process for Propionic Acid Production from Glycerol and Potato Juice Using High Cell Density Fermentation." Bioresource Technology, vol. 135, 2013, pp. 504-512.
Liu et al. "Glycerol/glucose Co-fermentation: One More Proficient Process to Produce Propionic Acid by Propionibacterium Acidipropionici." Current Microbiology, vol. 62, 2011, pp. 152-158.
Kosmider et al. "Propionic Acid Production by *Propionibacterium freudenreichii* ssp. Shermanii Using Crude Glycerol and Whey Lactose Industrial Wastes." Polish Journal of Environmental Studies, vol. 19, 2010, pp. 1249-1253.
Jiang et al. "Enhanced propionic acid production from whey lactose with immobilized Propionibacterium acidipropionici and the role of trehalose synthesis in acid tolerance." Green Chemistry, vol. 17, 2015, pp. 250-259.
Duarte et al.; "Microbial production of Propionic and Succinic acid from Sorbitol using Propionibacterium acidipropionici." AMB Express, 2015, vol. 5, pp. 1-8.
Zhu et al. "Optimization and scale-up of propionic acid production by propionic acid-tolerant Propionibacterium acidipropionici with glycerol as the carbon source." Bioresource Technology, vol. 101, 2010, pp. 8902-8906.
Apr. 26, 2016 International Search Report issued in International Patent Application No. PCT/EP2016/055753.
Apr. 26, 2016 Written Opinion issued in International Patent Application No. PCT/EP2016/055753.
Office Action issued in Colombian Application No. NC2017/0009093.
Boyaval et al. "Production of propionic acid." Lait, 1995, vol. 75, No. 4-5, pp. 453-461, doi: https://doi.org/10.1051/lait:19954-535.

* cited by examiner

*Primary Examiner* — Hamid R Badr
(74) *Attorney, Agent, or Firm* — Oliff PLC

(57) ABSTRACT

A process for manufacturing propionate products through fermentation, including the steps of fermenting a carbon source selected from sugars and lactate in a fermentation medium by means of a propionic acid producing microorganism to provide a first fermentation broth comprising a propionate salt, recovering propionic acid producing microorganism from the first fermentation broth, subjecting the first fermentation broth from which propionic acid producing microorganism have been recovered to a water removal step to form a first propionate salt product, fermenting a carbon source comprising glycerol with the propionic acid producing microorganism recovered from the first fermentation broth in the presence of an inorganic alkaline salt to provide a second fermentation broth comprising a propionate salt, subjecting the second fermentation broth to a purification step comprising at least one precipitation step, to form a second propionate salt product. The process allows efficient manufacture of propionate salts products.

13 Claims, No Drawings

PROCESS FOR MANUFACTURING PROPIONATE PRODUCTS

The present invention pertains to a process for manufacturing propionate products via a fermentation process.

Propionic acid can be manufactured through fermentation of a carbon source using a microorganism. For example, Zhu et al (Bioresource Technology 101 (2010) 8902-8902) describes a fermentation process for the manufacture of calcium propionate wherein glycerol is fermented using *Propionibacterium acidipropionici*. Calcium hydroxide is added during the fermentation to neutralize the acid generated during the fermentation, resulting in the formation of calcium propionate.

Propionate salts are attractive for many purposes. For example they are attractive for use in feed and food preservation, where they provide long lasting broad spectrum activity. Most important salts in this respect are calcium, sodium, potassium, and ammonium salts. The calcium salt is considered of particular interest. The propionate salt may be used in solution, or in the form of a solid salt.

A problem which has been found to occur in the preparation of propionate salts via fermentation resides in the complexity of the fermentation process, both as regards carbon sources which can be fermented, and as regards side products which are formed during fermentation. There is need in the art for a fermentation process for manufacturing propionate salts which combines a high yield of propionate salt with an efficient growth of the microorganism and the possibility of obtaining a high-purity propionate salt product.

The present invention provides a process which solves this problem.

The present invention pertains to a process for manufacturing propionate products through fermentation, comprising the steps of fermenting a carbon source selected from sugars and lactate in a fermentation medium by means of a propionic acid producing microorganism to provide a first fermentation broth comprising a propionate salt, recovering propionic acid producing microorganism from the first fermentation broth, subjecting the first fermentation broth from which propionic acid producing microorganism have been recovered to a water removal step to form a first propionate salt product, fermenting a carbon source comprising glycerol with the propionic acid producing microorganism recovered from the first fermentation broth in the presence of an inorganic alkaline salt to provide a second fermentation broth comprising a propionate salt, subjecting the second fermentation broth to a purification step comprising at least one precipitation step, to form a second propionate salt product.

In the process according to the invention, there are two sequential fermentation steps. In the first fermentation step, a carbon source selected from sugars and lactate is fermented under the formation of a propionate salt product stream. This step may also be indicated herein as the sugar fermentation step. Then, the microorganisms obtained in the sugar fermentation step are recovered and used to ferment a carbon source comprising glycerol, to form a further propionate salt product stream. The two propionate salt product streams are processed separately.

By applying two different fermentations, i.e. a sugar-based fermentation and a glycerol-based fermentation, and treating the resulting streams separately, it has been found that it is possible to benefit from the advantageous effects of both types of fermentation. More specifically, it has been found that sugar fermentation can result in efficient cell growth, which makes for a large yield of biomass. The resulting product, however, may be relatively difficult to purify due to the presence of substantial amounts of acetate anions. In contrast, the glycerol fermentation yields a product which can be purified to high purity propionate salt products. However, the glycerol fermentation results only in limited biomass formation. By combining the fermentations in the manner prescribed, an efficient process is obtained. Further advantages of the process according to the invention will be discussed below.

The process according to the invention will be discussed in more detail below.

The first step in the process according to the invention is fermenting a carbon source selected from sugars and lactate in a fermentation medium by means of a propionic acid producing microorganism to provide a first fermentation broth comprising a propionate salt.

Fermentation processes for the manufacture of propionate are known in the art and require no further elucidation here. It is within the scope of the skilled person to select, using his common general knowledge, a suitable fermentation process, including fermentation conditions, and a suitable microorganism. In the selection of the microorganism, care should be taken to select an organism which is capable of fermenting sugars or lactate (in the first fermentation step of the process according to the invention) and glycerol (in the second fermentation step of the process according to the invention).

The carbon source used in the first step of the process according to the invention is selected from sugars and lactate. Examples of suitable sugars and sources of sugar include glucose, sucrose, dextrose syrup, starch, hydrolysed starch, cellulose, hydrolysed cellulose, molasses, xylose, lignocellulose hydrolysates, lactose and whey. Suitable lactate sources are sodium lactate, potassium lactate, ammonium lactate, magnesium lactate, calcium lactate, and lactic acid. Of the lactate sources, the use of calcium lactate may be preferred, since this will result in the formation of calcium propionate, which is a preferred product of the invention. From a production point of view glucose, lactate, and sucrose may be preferred. From an availability point of view, sources like molasses and starch may be preferred.

At least when the carbon source is selected from sugars the fermentation is carried out in the presence of an inorganic alkaline salt. This alkaline salt is present to ensure that the pH during the fermentation does not decrease to an unacceptable extent due to the manufacture of the propionic acid. Where the carbon source is a lactate salt, the addition of an inorganic base may not always be required because lactate is converted into propionate, which does not have a pH effect. Nevertheless, also in that case, an inorganic base may be added for pH adjustment.

Suitable bases include hydroxides, oxides, and carbonates of calcium, magnesium, sodium, and potassium, resulting in the formation of a fermentation broth containing respectively calcium propionate, magnesium propionate, sodium propionate, or potassium propionate. It is preferred within the process according to the invention to use an alkaline calcium salt, as this results in the formation of calcium propionate, which is a preferred product according to the invention. Suitable alkaline calcium salts include hydroxides, oxides, and carbonates of calcium.

The next step is the removal of microorganism from the thus formed first fermentation broth. This step can be carried out when sufficient biomass has been formed for the following glycerol fermentation step. As the microorganism is to be used in a further fermentation, care should be taken to isolate the microorganisms under such conditions that the organism is kept alive. Taking this into account, the removal of microorganism may be carried out in manners known in the art, e.g., via filtration step or centrifugation step.

In the sugar fermentation, the weight of the biomass has increased, with the amount of biomass recovered being generally at least 10 times the weight of the biomass originally added, in particular at least 20 times, sometimes even at least 100 times. In the present specification the weight of the biomass is calculated as dry weight, unless expressly indicated otherwise.

It is preferred for the removal of microorganisms from the first fermentation broth to be carried out in a relatively high yield. There are two reasons for this. In the first place, the biomass is intended to be used in the subsequent glycerol fermentation. Further, biomass remaining in the fermentation broth may affect the properties of the product manufactured from this broth, e.g. in the form of a detrimental effect on product color. It is considered preferred for the biomass to be removed so that the resulting product has a turbidity of at most 1000 NTU, in particular at most 500 NTU, more specifically at most 200 NTU. A turbidity of at most 100 NTU is preferred.

In a further step of the process according to the invention, the first fermentation broth from which propionic acid producing microorganism have been recovered is subjected to a water removal step to form a first propionate salt product, in particular a calcium propionate product. This water removal step can be carried out in a number of ways.

In a first embodiment, the first fermentation broth from which propionic acid producing microorganism have been recovered is subjected to a water removal step in its entirety. In this case, a first propionate salt product is formed which comprises all matter present in the first fermentation broth from which propionic acid producing microorganism have been recovered, including remaining nutrients. This drying step can be carried out in manners known in the art for water removal, including spray drying, drum vacuum drying, thin film drying, e.g., agitated thin film drying, mechanically agitated drying, spray granulation, and freeze drying.

The resulting product is a solid material, in particular a solid particulate material, with a propionate salt content in the range of 30-70 wt. %, in particular 40-60 wt. %, of propionate salt, in particular calcium propionate, with the remainder comprising one or more of further salts of carboxylic acids, in particular succinate and/or acetate salts, and further components resulting from, e.g., the biomass and residual medium/nutrient components. In one embodiment, the resulting product comprises acetate salt in the range of 3-20 wt. %, in particular 8-15 wt. %, more in particular 10-13 wt. % and/or succinate salt in an amount of 0-10 wt. %, in particular 3-6 wt. %. It is preferred for calcium propionate, calcium succinate, and calcium acetate to make up at least 85 wt. % of the total first calcium propionate product, obtained in this manner, in particular at least 90 wt. %, more in particular between 90 and 98 wt. %. In the above, the percentages are calculated as anion (acetate, succinate, propionate) on the total anhydrous solid material.

It is noted that it is possible to include other components in the fermentation broth before spray drying, e.g., additional carboxylic acid salts such as lactates or acetates, carriers like maltodextrin, starch, milk solids, whey, flour or other functional ingredients like green tea extract, nisin, and rosemary extract. This may be attractive if it is desired to manufacture a product with a particular composition.

In another embodiment, the step of subjecting the first fermentation broth from which propionic acid producing microorganism have been recovered is carried out by a process encompassing precipitation of a propionate salt, in particular calcium propionate from the first fermentation broth. Precipitation may be initiated by concentration and other measures known to improve the yield of a precipitation step, e.g., reduction of temperature or addition of compounds which reduce solubility. Precipitation can be performed batchwise or continuous, in a single step or in multiple steps.

The precipitated propionate salt product, in particular calcium propionate is separated from the aqueous medium. This can be done by methods known in the art, including one or more of filtration, centrifugation, decantation, etc. It is within the scope of the skilled person to select a suitable manner. If so desired, the propionate salt product can be washed to increase product purity. The washing liquid, if used, can, e.g., be water or a propionate salt solution. The washing liquid can be recycled to obtain a high yield. The solid calcium propionate product can be dried as desired.

In this embodiment it is possible to precipitate all types of carboxylate salts, in particular calcium carboxylate salts present in the system, in particular calcium propionate in combination with calcium succinate (if present) and/or calcium acetate (if present). In this case, a final product may, e.g., be obtained with a propionate salt content, in particular calcium propionate in the range of 30-80 wt. %, in particular 40-70 wt. %, acetate salt, in particular calcium acetate in the range of 3-20 wt. %, in particular 8-15 wt. %, more in particular 10-13 wt. % and succinate salt, in particular calcium succinate, in an amount of 0-10 wt. %, in particular 3-6 wt. %. It is preferred for calcium propionate, calcium succinate, and calcium acetate to make up at least 85 wt. % of the total first calcium propionate product, obtained in this manner, in particular at least 90 wt. %, more in particular at least 95%. In the above, the percentages are calculated as anion (acetate, succinate, propionate) on the total anhydrous solid material.

It is also possible to sequentially precipitate succinate salts and propionate salts from the first fermentation broth, this can, e.g., be done via a process for manufacturing a solid propionate salt from a mixture comprising propionate and succinate comprising the steps of providing an aqueous medium comprising succinate anions and propionate anions, providing an inorganic soluble salt in the aqueous medium in such an amount that the majority of succinate ions is converted to solid succinate salt while the majority of propionate ions remains in solution, separating the aqueous medium comprising the majority of propionate ions from the solid succinate salt, increasing the concentration of salt in the aqueous medium to convert the majority of propionate ions to solid propionate salt, separating the solid propionate salt from the aqueous medium.

As indicated above, the propionic acid producing microorganism is recovered from the first fermentation broth. In a next step in the process according to the invention, a carbon source comprising glycerol is fermented with the propionic acid producing microorganism recovered from the first fermentation broth in the presence of an alkaline salt to provide a second fermentation broth comprising a propionate salt.

Fermentation processes for the manufacture of propionic acid starting from a carbon source comprising glycerol are known in the art and require no further elucidation here. It is within the scope of the skilled person to select, using his common general knowledge, a suitable fermentation process, including fermentation conditions.

The carbon source used in this fermentation step comprises glycerol. It has been found that the use of glycerol as carbon source makes it possible to obtain a fermentation process which generates relatively high amounts of propionate salt, in particular calcium propionate in combination with relatively low amounts of acetate salts. This is attractive because the separation of propionate salts and acetate salts is generally complicated. It is preferred for the carbon source to consist for at least 70 wt. % of glycerol, more in particular at least 80 wt. %, still more in particular at least 90 wt. %, calculated on the total amount of carbon source provided during the fermentation.

A base is added during the fermentation step to compensate for the pH decrease which would occur due to the production of the carboxylic acids.

Suitable bases include hydroxides, oxides, and carbonates of calcium, magnesium, sodium, and potassium, resulting in the formation of a fermentation broth containing respectively calcium propionate, magnesium propionate, sodium propionate, or potassium propionate. It is preferred within the process according to the invention to use an alkaline calcium salt, as this results in the formation of calcium propionate, which is a preferred product according to the invention. Suitable alkaline calcium salts include hydroxides, oxides, and carbonates of calcium.

The alkaline salts used in the two fermentation steps may be the same or different. For reasons of efficiency it may be preferred for the alkaline salt provided in the fermenting of a carbon source selected from sugars and lactate and the alkaline salt provided in the fermenting of a carbon source comprising glycerol to be salts of the same cation. The use of calcium salts is particularly preferred.

Once the fermentation has run to the desired extent, the second fermentation broth is subjected to a purification step comprising at least one precipitation step, to form a second calcium propionate product.

In general, the second fermentation broth is subjected first to a biomass removal step, which can be carried out in manners known in the art. Reference is made to what is stated above for the removal of biomass from the first fermentation broth. As for the step described above, it is considered preferred for the biomass to be removed so that the resulting product has a turbidity of at most 1000 NTU, in particular at most 500 NTU, more specifically at most 200 NTU. A turbidity of at most 100 NTU is preferred. It has been found that the presence of biomass may interfere with the further precipitation step in the process according to the invention. The biomass isolated in this step may be provided to a second glycerol-based fermentation, if this is desired.

The resulting broth from which biomass has been removed is subjected to at least one precipitation step, to form a second propionate salt product.

Before the precipitation step, the medium may if so desired be contacted with an adsorbent, in particular an active carbon adsorbent, to remove impurities.

The precipitation step can be carried out as described above. Precipitation may be initiated by concentration of the medium, and/or by other measures known to improve the yield of a precipitation step, e.g., reduction of temperature or addition of compounds which reduce solubility. Reference is made to what has been stated above on the precipitation step.

The precipitated propionate salt product, in particular calcium propionate is separated from the aqueous medium. This can be done by methods known in the art, including one or more of filtration, centrifugation, decantation, etc. It is within the scope of the skilled person to select a suitable manner. If so desired, the propionate salt product can be washed to increase product purity. The washing liquid, if used, can, e.g., be water or a propionate salt solution. The washing liquid can be recycled to obtain a high yield. The solid propionate salt product can be dried as desired.

In one embodiment, in addition to propionate salts, other carboxylate salts, in particular succinate and/or acetate salts are also precipitated. In particular calcium carboxylate salts present in the system may be precipitated together, in particular calcium propionate in combination with calcium succinate (if present) and/or calcium acetate (if present). In this case, a final product may, e.g., be obtained with a propionate salt content, in particular calcium propionate in the range of 50-90 wt. %, in particular 60-80 wt. %, more in particular 70-80 wt. %, acetate salt, in particular calcium acetate in the range of 0-5 wt. %, in particular 0-2 wt. %, and succinate salt, in particular calcium succinate, in an amount of 0-20 wt. %, in particular 0-10 wt. %, more in particular 0-5 wt. %. It is preferred for calcium propionate, calcium succinate, and calcium acetate to make up at least 85 wt. % of the total first calcium propionate product, obtained in this manner, in particular at least 90 wt. %, more in particular at least 95%. In the above, the percentages are calculated as anion (acetate, succinate, propionate) on the total anhydrous solid material.

It is also possible to sequentially precipitate succinate salts and propionate salts from the second fermentation broth, this can, e.g., be done via a process for manufacturing a solid propionate salt from a mixture comprising propionate and succinate comprising the steps of provideing an aqueous medium comprising succinate anions and propionate anions, providing an inorganic soluble salt in the aqueous medium in such an amount that the majority of succinate ions is converted to solid succinate salt while the majority of propionate ions remains in solution, separating the aqueous medium comprising the majority of propionate ions from the solid succinate salt, increasing the concentration of salt in the aqueous medium to convert the majority of propionate ions to solid propionate salt, separating the solid propionate salt from the aqueous medium.

It will be clear to the skilled person that the various embodiments and preferences describes herein can be combined, unless they are presented as mutually excluding alternatives.

The present invention will be elucidated by the following examples, without being limited thereto or thereby.

EXAMPLE 1: GLUCOSE FERMENTATION FOLLOWED BY GLYCEROL FERMENTATION

A fermenter comprising 5 kg medium was inoculated with a culture of *Propionibacterium acidipropionici*. The medium contained 80 g/kg glucose and 52 g/kg YEP (yeast extract paste, 50% dry solids). The fermenter was operated at 30° C. and with a pH of 6.5. The pH was controlled by adding Ca(OH)2 solution. After ±45 hours the fermentation was stopped. The fermentation broth was centrifuged at 5000 RPM. The microorganism was present in the sediment of the centrifugation step.

In this step, the amount of biomass was increased from 20 gram added initially to 150 gram harvested, both calculated as dry weight.

24 grams of biomass was added to a fermenter comprising 1 kg medium containing 80 g/kg glycerol and 52 g/kg YEP. The fermenter was operated at 30° C. and with a pH of 7.0. The pH was controlled by adding Ca(OH)2 solution.

The fermentation yielded a volumetric productivity of 1.2 gram calcium propionate per kilogram medium per hour. The total yield of the fermentation was 72 wt. %, calculated as grams propionate per gram glycerol.

EXAMPLE 2: WORK-UP OF GLUCOSE FERMENTATION BROTH

A glucose fermentation was carried out analogous to that described in the first paragraph of Example 1. The biomass was isolated therefrom by centrifugation as described therein. 1000 grams of the remaining fermentation broth was dried using a rotary evaporator, first under atmospheric pressure, then under vacuum. After 6 hours, a dry product was obtained.

The fermentation broth comprised the following organic acids, as determined using GC

TABLE 1

GC organic acids in fermentation broth

| component | | |
|---|---|---|
| formic acid | [% (w/w)] | <0.02 |
| acetic acid | [% (w/w)] | 0.57 |
| propionic acid | [% (w/w)] | 2.4 |
| ethanol | [% (w/w)] | <0.02 |
| maleic acid | [% (w/w)] | <0.01 |
| oxalic acid | [% (w/w)] | <0.01 |
| sorbic acid | [% (w/w)] | <0.01 |
| fumaric acid | [% (w/w)] | <0.01 |
| succinic acid | [% (w/w)] | 0.24 |
| lactic acid | [% (w/w)] | 0.02 |
| pyruvic acid | [% (w/w)] | <0.03 |
| 2-hydroxy butyric acid | [% (w/w)] | <0.01 |

The solid product after the drying step had the following composition:

TABLE 2 composition of solid product

| component | | |
|---|---|---|
| propionic acid | [% (w/w)] | 36 |
| acetic acid | [% (w/w)] | 9.2 |
| succinic acid | [% (w/w)] | 4.2 |
| calcium | [% (w/w)] | 18.2 |
| water | [% (w/w)] | 16.5 |
| further solids | | balance |

This example illustrates the step of water removal to form a first calcium propionate product. In commercial operation, the water removal step will be carried out by other methods, e.g., spray drying, but analogous results may be obtained.

EXAMPLE 3: WORK-UP OF GLYCEROL FERMENTATION BROTH

A glycerol fermentation broth obtained analogous to the second paragraph of Example 1 is processed as follows:

The fermentation broth obtained from the glycerol fermentation was subjected to a centrifugation step at 5000 RPM. The sediment of the centrifugation step was the microorganism. The supernatant was processed further.

To the supernatant, active carbon was added in an amount of 0 wt. % per gram of calcium propionate, 0.1 wt. % per gram of calcium propionate, or 10 wt. % per gram of calcium propionate. The fermentation broth to which active carbon was added was kept for one hour at 60° C. The active carbon was removed by vacuum filtration using a 0.2 micron filter.

As can be seen from the following Table, an active carbon treatment did not result in the removal of calcium propionate from the system:

| Starting materials | Ca propionate [% w/w] | Ca succinate [% w/w] | Ca acetate [% w/w] | Glycerol [% w/w] |
|---|---|---|---|---|
| 102° C. - no active carbon | 5.35 | 0.22 | <1 | <0.15 |
| 102° C. - 0.1 (% w/w) carbon | 5.35 | 0.23 | <1 | <0.15 |
| 102° C. - 10 (% w/w) carbon | 5.48 | 0.23 | <1 | <0.15 |

Solid calcium propionate was precipitated from the purified fermentation medium by concentrating the medium through evaporation of water. Evaporation was carried out at 102-103° C. (medium temperature) in an oil bath of 150° C. under atmospheric pressure. After about two hours, nucleation occurred, as could be seen from the formation of a haze. At that point in time, the temperature of the oil bath was reduced to 120° C. to reduce the evaporation rate during crystallization. Some cool oil was added to the oil bath to accelerate the reduction in temperature. About one hour after the start of the nucleation, the evaporation was stopped.

The crystals were separated from the liquid using vacuum filtration or centrifugation.

Active carbon treatment resulted in a substantial decrease in color of the starting material for the evaporation step. Additionally, during the evaporation step, the solution darkened. This effect was much more pronounced for the sample which had not been subjected to an evaporation step than for the sample which had been subjected to the evaporation step. This can be seen from the APHA values in the following table.

| Activated carbon (% w/w) | Starting material [APHA] | Material obtained [APHA] |
|---|---|---|
| 0 | 280 | 6600 |
| 0.1 | 110 | 4200 |
| 10 | <5 | 1900 |

The solid product obtained from the samples subjected to an active carbon treatment also had a much better color than the product obtained from the sample wherein no active carbon treatment was carried out.

The composition of the products was as follows:

| Wet cake samples | S/L separation | Ca propionate [% w/w] | Ca succinate [% w/w] | Ca acetate [% w/w] | Glycerol [% w/w] | MC loss at 80° C.[1] |
|---|---|---|---|---|---|---|
| 102° C.- blank | Vacuum filtration (Buchner | 58.62 | 1.21 | 1.21 | <0.1 | 35% |

-continued

| Wet cake samples | S/L separation | Ca propionate [% w/w] | Ca succinate [% w/w] | Ca acetate [% w/w] | Glycerol [% w/w] | MC loss at 80° C.[1] |
|---|---|---|---|---|---|---|
| | funnel, 4-7 μm )) | | | | | |
| 102° C.-blank | Centrifuge (5000 rpm, 100 μm pore size, 1 minute) | 76.46 | 0.47 | 1.21 | <0.15 | 16% |
| 102° C.-0.1 (% w/w) carbon | Centrifuge (10000 rpm, 100 μm pore size, 1 minute | 87.92 | 0.28 | 1.34 | <0.1 | 10% |
| 102° C.-10 (% w/w) carbon | Vacuum filtration (Buchner funnel, 4-7 μm ) | 61.16 | 1.61 | 1.21 | <0.1 | 25% |

[1] MC loss at 80° C. stands for the moisture content of the materials, determined by keeping the material for 16 hours in an oven at a temperature of 80° C.

As can be seen from the above table, the use of a centrifuge for solid liquid separation gave better results than the use of a vacuum funnel. The relevancy of this result for commercial scale operation is limited.

The wet products were dried at 80° C. for 16 hours to form a dried product.

The invention claimed is:

1. A process for manufacturing propionate salts through fermentation, comprising the steps of
   fermenting a carbon source selected from sugars and lactate in a fermentation medium by means of a propionic acid producing microorganism to provide a first fermentation broth comprising a propionate salt,
   recovering propionic acid producing microorganism from the first fermentation broth,
   subjecting the first fermentation broth from which propionic acid producing microorganism have been recovered to a water removal step to form a first propionate salt,
   fermenting a carbon source comprising glycerol with the propionic acid producing microorganism recovered from the first fermentation broth in the presence of an inorganic alkaline salt to provide a second fermentation broth comprising a propionate salt,
   subjecting the second fermentation broth to a purification step comprising at least one precipitation step, to form a second propionate salt.

2. The process according to claim 1, wherein the propionate salt generated in the first and the second fermentation broth are salts of the same cation.

3. The process according to claim 1, wherein the carbon source is selected from the group consisting of glucose, lactate, sucrose and combinations thereof.

4. The process according to claim 1, wherein in the step of fermenting a carbon source selected from sugars and lactate, the weight of the biomass has increases in such a manner that the amount of biomass recovered is generally at least 10 times the weight of the biomass originally added.

5. The process according to claim 1, wherein the first fermentation broth from which propionic acid producing microorganism have been recovered is subjected to a water removal step in its entirety.

6. The process according to claim 1, wherein the step of subjecting the first fermentation broth from which propionic acid producing microorganism have been recovered is carried out by a process comprising precipitation of a propionate salt from the first fermentation broth.

7. The process according to claim 1, wherein the carbon source comprising glycerol contains at least 70 wt. % of glycerol calculated on the total amount of carbon source provided during the fermentation.

8. The process according to claim 1, wherein the second fermentation broth is subjected first to a biomass removal step.

9. The process according to claim 1, wherein in addition to propionate salts, other carboxylate salts are also precipitated.

10. The process according to claim 1, wherein succinate salts and propionate salts are precipitated sequentially from the second fermentation broth.

11. The process according to claim 9, wherein a product comprising
   70-80 weight percent (wt %) of a calcium propionate,
   0-5 wt % of a calcium acetate, and
   0-10 wt % of a calcium succinate salt,
is precipitated, where the calcium propionate, the calcium acetate, and the calcium succinate make up at least 85 wt % of the precipitated product, the percentages being calculated based on the respective anion of the total anhydrous solid material.

12. The process according to claim 9, wherein a product comprising
   70-80 weight percent (wt %) of a calcium propionate,
   0-5 wt % of a calcium acetate, and
   0-20 wt % of a calcium succinate salt,
is precipitated, where the calcium propionate, the calcium acetate, and the calcium succinate make up at least 95 wt % of the precipitated product, the percentages being calculated based on the respective anion of the total anhydrous solid material.

13. The process according to claim 9, wherein a product comprising
   70-80 weight percent (wt %) of a calcium propionate,
   0-2 wt % of a calcium acetate, and
   0-5 wt % of a calcium succinate salt,
is precipitated, the percentages being calculated based on the respective anion of the total anhydrous solid material.

* * * * *